United States Patent
Croft

(10) Patent No.: US 11,730,559 B2
(45) Date of Patent: Aug. 22, 2023

(54) RF TAG WITH GRAVITATIONALLY ALIGNED ORIENTATION

(71) Applicant: Covidien LP, Mansfield, MA (US)

(72) Inventor: Richard L. Croft, Mead, CO (US)

(73) Assignee: COVIDIEN LP, Mansfield, MA (US)

( * ) Notice: Subject to any disclaimer, the term of this patent is extended or adjusted under 35 U.S.C. 154(b) by 262 days.

(21) Appl. No.: 17/099,866

(22) Filed: Nov. 17, 2020

(65) Prior Publication Data

US 2021/0177537 A1 Jun. 17, 2021

Related U.S. Application Data

(60) Provisional application No. 62/948,385, filed on Dec. 16, 2019.

(51) Int. Cl.

| | |
|---|---|
| *A61B 90/00* | (2016.01) |
| *G16H 40/67* | (2018.01) |
| *G06K 19/02* | (2006.01) |
| *G06K 19/07* | (2006.01) |
| *A61L 31/14* | (2006.01) |
| *A61L 31/04* | (2006.01) |
| *A61B 34/20* | (2016.01) |
| *A61B 90/98* | (2016.01) |

(52) U.S. Cl.
CPC .............. *A61B 90/08* (2016.02); *A61B 34/20* (2016.02); *A61B 90/98* (2016.02); *A61L 31/042* (2013.01); *A61L 31/145* (2013.01); *G06K 19/02* (2013.01); *G06K 19/0723* (2013.01); *G16H 40/67* (2018.01); *A61B 2034/2072* (2016.02); *A61B 2090/0805* (2016.02); *A61B 2090/3975* (2016.02)

(58) Field of Classification Search
CPC ......... A61B 90/08; A61B 34/20; A61B 90/98; A61B 2034/2072; A61B 2090/0805; A61B 2090/3975; A61B 2090/397; A61L 31/042; A61L 31/145; G06K 19/02; G06K 19/0723; G16H 40/67; G16H 20/40

See application file for complete search history.

(56) References Cited

U.S. PATENT DOCUMENTS

| | | |
|---|---|---|
| 6,026,818 A | 2/2000 | Blair et al. |
| 2004/0250819 A1 | 12/2004 | Blair et al. |
| 2008/0021308 A1* | 1/2008 | Dimmer ................. A61B 5/062 600/424 |

(Continued)

*Primary Examiner* — Zhitong Chen
(74) *Attorney, Agent, or Firm* — Carter, DeLuca & Farrell, LLP

(57) ABSTRACT

A transponder includes an encapsulant defining a cavity having a spherical internal profile. A suspension medium and a core are contained within the cavity. The core includes a rod having a first end and a second end, and defines a longitudinal axis between the first end and the second end. The longitudinal axis of the rod defines an axis of sensitivity of the transponder, and the core defines a center of gravity closer to the second end of the rod as compared to the first end of the rod. The center of gravity is disposed along the longitudinal axis of the rod. The transducer includes a conductive coil wrapped around the rod, and a capacitor coupled to the conductive coil. The core self-orients itself such that the axis of sensitivity of the transponder is parallel with a plumb to gravity axis.

20 Claims, 2 Drawing Sheets

(56) References Cited

U.S. PATENT DOCUMENTS

| | | | | |
|---|---|---|---|---|
| 2011/0282175 A1* | 11/2011 | Geissler | ............... | A61B 5/0031 |
| | | | | 600/365 |
| 2012/0199658 A1* | 8/2012 | Kaga | ....................... | B28B 23/00 |
| | | | | 235/492 |
| 2017/0169172 A1* | 6/2017 | Blair | ....................... | G16H 40/40 |
| 2018/0333309 A1* | 11/2018 | Merritt | ................... | A61B 90/90 |

\* cited by examiner

RF TAG WITH GRAVITATIONALLY ALIGNED ORIENTATION

CROSS-REFERENCE TO RELATED APPLICATIONS

This application claims the benefit of and priority to U.S. Provisional Patent Application Ser. No. 62/948,385 filed Dec. 16, 2019, the entire disclosure of which is incorporated by reference herein.

TECHNICAL FIELD

This disclosure relates generally to radio-frequency (RF) tags, and more particularly, to RF tags for use with surgical objects and devices used in body cavities during surgery, which RF tags have a gravitationally aligned orientation.

BACKGROUND

It is often useful or important to determine whether objects associated with a surgery are present in a patient's body before completion of the surgery. Such objects may take a variety of forms. For example, the objects may take the form of instruments, for instance scalpels, scissors, forceps, hemostats, and/or clamps. Also for example, the objects may take the form of related accessories and/or disposable objects, for instance surgical sponges, gauzes, and/or pads. Failure to locate an object before closing the patient may require additional surgery, and in some instances may have serious adverse medical consequences.

Some hospitals have instituted procedures which include checklists or requiring multiple counts to be performed to track the use and return of objects during surgery. Such a manual approach is inefficient, requiring the time of highly trained personnel, and is prone to error.

Another approach employs transponders and a wireless interrogation and detection system. Such an approach employs wireless transponders (e.g., RF tags) which are attached to various objects used during surgery. The interrogation and detection system includes a transmitter that emits pulsed wideband wireless signals (e.g., radio or microwave frequency) and a detector for detecting wireless signals returned by the transponders in response to the emitted pulsed wideband signals. Such an automated system may advantageously increase accuracy while reducing the amount of time required of highly trained and highly compensated personnel. Examples of such an approach are discussed in U.S. Pat. No. 6,026,818, issued Feb. 22, 2000, and U.S. Patent Publication No. US 2004/0250819, published Dec. 16, 2004.

Commercial implementation of such an automated system requires that the overall system be cost competitive and highly accurate. In particular, false negatives must be avoided to ensure that objects are not mistakenly left in the patient. Some facilities may wish to install a single interrogation and detection system in each surgery theater, while other facilities may move an interrogation and detection system between multiple surgical theaters. In either case, the overall system will require a large number of transponders, since at least one transponder is carried, attached or otherwise coupled to each object which may or will be used in surgery. Consequently, the transponders must be inexpensive. However, inexpensive transponders typically have a relatively large variation in the frequency of signals they emit, making it difficult to accurately detect the signals returned by the transponders. This may be particularly difficult in some environments which are noisy with respect to the particular resonant frequencies of the transponders. Consequently, a new approach to detection of the presence and absence of transponder that facilitates the use of inexpensive transponders is highly desirable.

When trying to locate an RF tagged item it is important for the detection antennas and or the electromagnetic fields to be aligned with the axis of sensitivity of the RF tags. In most cases the orientation of the RF tag (and tagged item) in three dimensional space is unknown and uncontrolled requiring scanning motion or complex antenna geometry to provide adequate detection coverage.

Accordingly, it is desired to have an RF tag that aligns its axis of sensitivity with gravity.

SUMMARY

This disclosure relates to RF tags for use with surgical objects and devices used in body cavities during surgery, which RF tags have a gravitationally aligned orientation.

According to an aspect of the disclosure, a transponder for use in a surgical environment and for detection by a detection system is provided. The transponder includes an encapsulant defining a cavity. A suspension medium and a core are contained within the cavity of the encapsulant. The core includes a ferrite rod having a first end and a second end, and defining a longitudinal axis between the first end and the second end. The longitudinal axis of the rod defines an axis of sensitivity of the transponder. A head is supported on the second end of the rod, and the rod and the head are configured to define a center of gravity proximate the second end or in the head, wherein the center of gravity is disposed along the longitudinal axis of the rod. A conductive coil is wrapped around the rod, and a capacitor is coupled to the conductive coil. The core is self-orienting such that the axis of sensitivity of the transponder is parallel with a plumb to gravity axis.

The ferrite rod, the conductive coil and the capacitor may form a series inductor/capacitor circuit.

According to another aspect of the present disclosure a transponder for use in a surgical environment and for detection by a detection system is provided. The transponder includes an encapsulant defining a cavity. A suspension medium and a core are contained within the cavity of the encapsulant. The core includes a rod having a first end and a second end, and defining a longitudinal axis between the first end and the second end, wherein the longitudinal axis of the rod defines an axis of sensitivity of the transponder. The core defines a center of gravity closer to the second end of the rod as compared to the first end of the rod, and the center of gravity is disposed along the longitudinal axis of the rod. The core further includes a conductive coil wrapped around the rod, and a capacitor coupled to the conductive coil. The core is self-orienting such that the axis of sensitivity of the transponder is parallel with a plumb to gravity axis.

The rod may be fabricated from a ferrous material. The rod, the conductive coil and the capacitor may form a series inductor/capacitor circuit.

According to yet another aspect of the present disclosure, a surgical article for placement in a cavity of a patient during surgery is provided. The surgical article includes a deformable object capable of absorbing body fluid, and a transponder connected to the deformable object.

The transponder includes an encapsulant defining a cavity. A suspension medium and a core are contained within the cavity of the encapsulant. The core includes a ferrite rod having a first end and a second end, and defining a longitudinal axis between the first end and the second end. The longitudinal axis of the rod defines an axis of sensitivity of the transponder, and the core defines a center of gravity closer to the second end of the rod as compared to the first end of the rod. The center of gravity is disposed along the longitudinal axis of the rod. The core further includes a conductive coil wrapped around the rod, and a capacitor coupled to the conductive coil. The core is self-orienting such that the axis of sensitivity of the transponder is parallel with a plumb to gravity axis.

The core may include a head supported on the second end of the rod.

The capacitor may be located proximate the second end of the rod.

The encapsulant may be fabricated from a bio-inert plastic. The encapsulant may have a spherical outer profile.

The suspension medium may include a pure silicone fluid, a silicone gel and/or a water cellulose mixture.

The head of the core may have a hemi-spherical outer profile.

The cavity of the encapsulant may have a spherical inner profile.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

Various embodiments of the presently disclosed RF tags, transponders, and articles containing them are described herein below with reference to the drawings, wherein.

DETAILED DESCRIPTION OF EMBODIMENTS

In the following description, certain specific details are set forth in order to provide a thorough understanding of disclosed embodiments. However, one skilled in the relevant art will recognize that embodiments may be practiced without one or more of these specific details, or with other methods, components, materials, etc. In other instances, well-known structures associated with transmitters, receivers, or transceivers have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

As used herein, the terms parallel and perpendicular are understood to include relative configurations that are substantially parallel and substantially perpendicular up to about + or −10 degrees from true parallel and true perpendicular.

The headings and Abstract of the Disclosure provided herein are for convenience only and do not interpret the scope or meaning of the embodiments.

Figure 1:
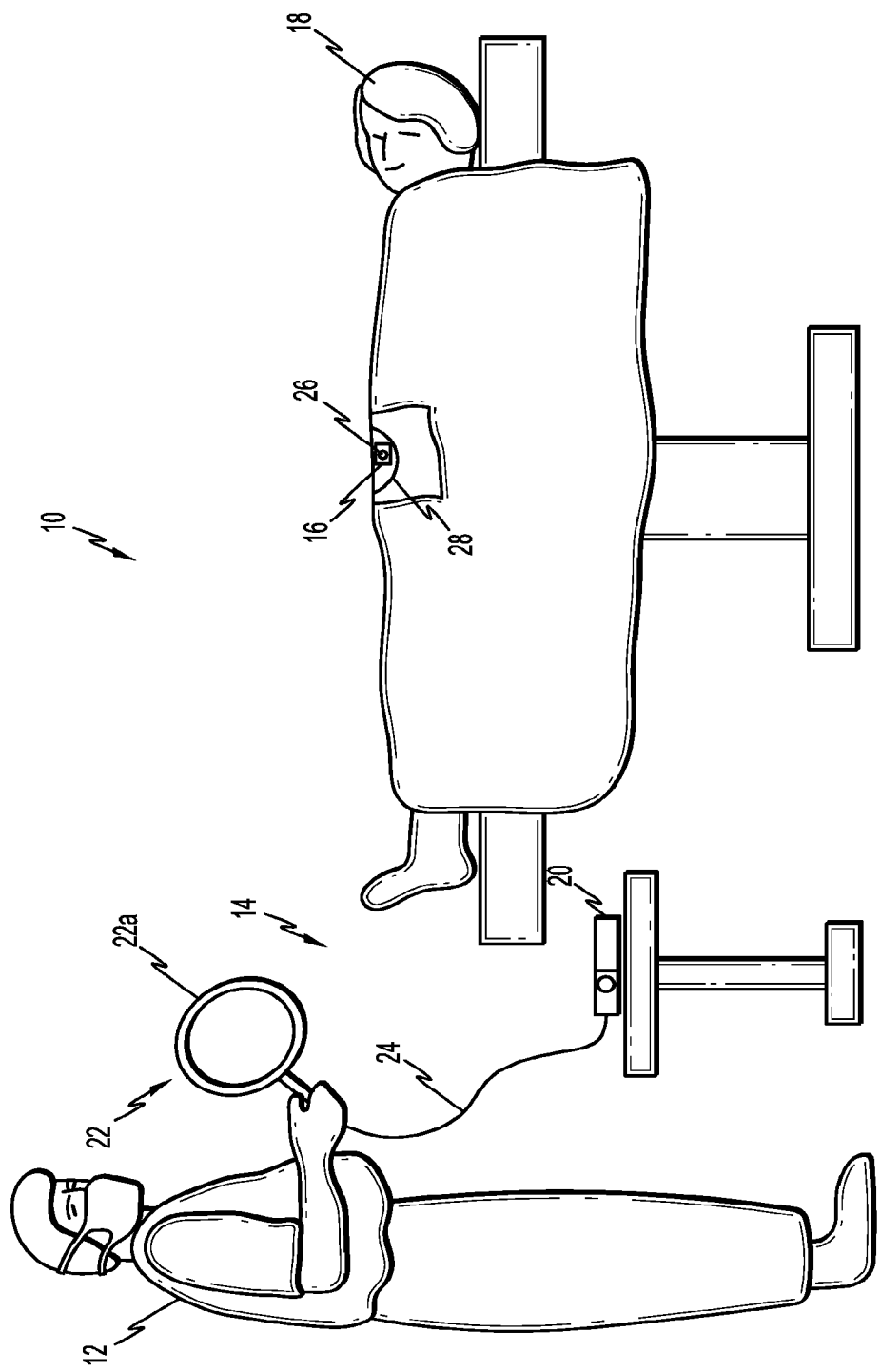
FIG. 1 is a schematic diagram showing a surgical environment illustrating a medical provider using an interrogation and detection system to detect an object in a patient that is tagged with a transponder according to one illustrated embodiment.

FIG. 1 depicts a surgical environment 10 in which a medical provider 12 operates an interrogation and detection system 14 to ascertain the presence or absence of objects 16 in, or on, a patient 18. The interrogation and detection system 14 may include a controller 20, and an antenna 22 coupled to the controller 20 by one or more communication paths, for example coaxial cable 24. The antenna 22 may take the form of a hand-held wand 22a.

The object 16 may take a variety of forms, for example instruments, accessories and/or disposable objects useful in performing surgical procedures. For instance, the object 16 may take the form of scalpels, scissors, forceps, hemostats, and/or clamps. Also for example, the objects 16 may take the form of surgical sponges, gauze and/or padding. The object 16 is tagged, carrying, attached or otherwise coupled to a transponder or RF tag 26. Embodiments of the interrogation and detection system 14 disclosed herein are particularly suited to operate with transponders 26 which are not accurately tuned to a chosen or selected resonant frequency. Consequently, the transponders 26 do not require high manufacturing tolerances or expensive materials, and thus may be inexpensive to manufacture.

In use, the medical provider 12 may position the wand 22 approximate the patient 18 in order to detect the presence or absence of the transponder 26 and hence an object 16. The medical provider 12 may in some embodiments move the wand 22a along and/or across the body of the patient 18. In some embodiments, the wand 22a may be sized to fit at least partially in a body cavity 28 of the patient 18.

Figure 2:
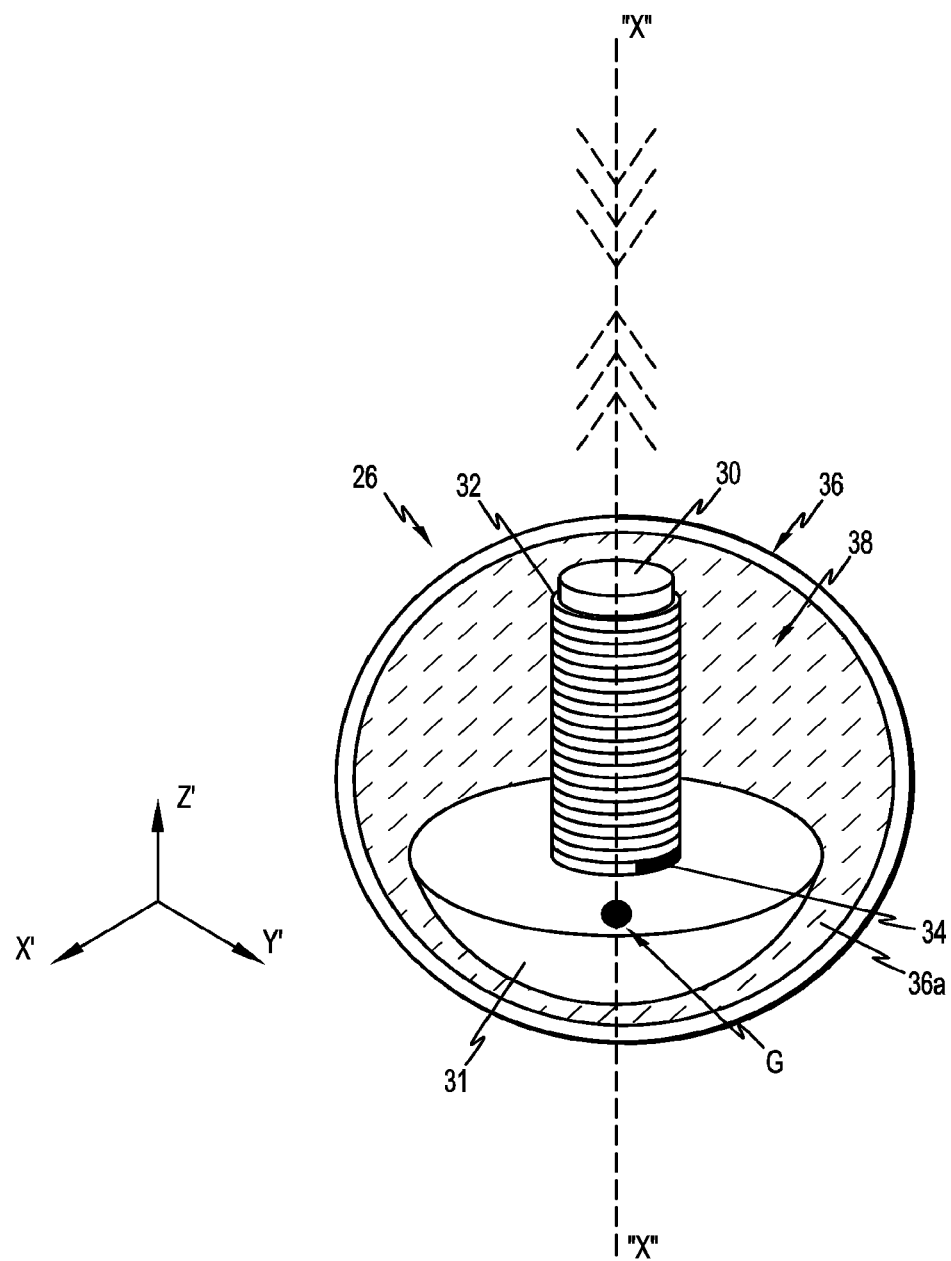
FIG. 2 is a schematic illustration of a transponder, according to one illustrated embodiment.

Turning to FIG. 2, a transponder 26, according to one illustrated embodiment, is shown. The transponder 26 includes a core 29 contained in an encapsulant 36. The core 29 of the transponder 26 includes a miniature ferrite rod 30 having a first or free end 30a, and second or supported end 30b integrally connected to or secured to an enlarged head 31. The head 31 of the core 29 of the transponder 26 may be fabricated from ferrite or other weighted materials, such as, for example, nickel-iron, cobalt-iron, iron and oxides of iron, ferrite, silicone-steel and/or amorphous metallic alloys. The rod 30 and the head 31 have a substantially mushroom-shaped profile. As so arranged and constructed, the core 29 of the transponder 26 defines a center of gravity (G) located proximate second end 30b of the rod 30, or within the head 31. It is contemplated that the head 31 may have a hemi-spherical outer profile.

The transponder 26 includes a conductive coil 32 wrapped about an exterior surface of the rod 30 to form an inductor (L), and a capacitor (C) 34 coupled to the conductive coil 32 to form a series LC circuit. The conductive coil 32 may, for example, take the form of a spiral wound conductive wire with an electrically insulative sheath or sleeve. The capacitor (C) 34 is disposed closer to second end 30b of the rod 30 as compared to first end 30a, in order to help maintain the center of gravity (G) closer to the head 31. However, it is contemplated that the capacitor (C) 34 may be disposed at any location along a length of the rod 30.

The rod 30 of the core 29 defines a longitudinal axis "X" which also defines an axis of sensitivity of the transponder 26. The sizes and configurations of the rod 30 and the head 31 are selected such that the center of gravity (G) of core 29 is disposed along the longitudinal axis "X".

The transponder 26, as mentioned above, includes an encapsulation 36 that encapsulates the rod 30, the conductive coil 32, and the capacitor 34. The encapsulant 36 may be a bio-inert plastic that protects the rod 30, the conductive coil 32, and/or the capacitor 34 from pressure and/or from fluids, for example bodily fluids. The encapsulant 36 may have a spherical profile. Specifically, the encapsulant 36 defines an inner cavity 36a having a spherical profile, while an outer profile of the encapsulant 36 can be spherical or any other functionally beneficial shape or configuration sufficiently large to permit core 29 to freely float, rotate or spin therein.

The inner cavity 36a of the encapsulant 36 is filled, at least partially, with a non-corroding suspension medium or fluid (F) 38 including and not limited to a pure silicone fluid, a silicone gel and/or a water methyl cellulose mixture.

As so constructed, the core 29 of the transducer 26 is suspended in the encapsulant 36 such that the center of gravity (G) of the core 29 forces the core 29 to orient itself such that the longitudinal axis "X" of the rod 30 (e.g., the axis of sensitivity of the transponder 26) is axially aligned with a plumb to gravity axis "Z'" (e.g., the core 29 is in an upright orientation).

In some embodiments, the transponder 26 may include eyelets, hooks, fastening features and the like that may be used to attach the transponder 26 to various types of objects 16, for example surgical sponges.

The transponder 26 may have a length of about 6-10 millimeters, specifically about 8 millimeters and a diameter of about 1.5-3 millimeters, specifically about 2 millimeters. Employing such small dimensions ensures that the transponder 26 does not impede deformation of objects 16 such as sponges.

The transponder 26 may include an optional diode (not shown), to protect against over-voltage occurrences caused by other electronic instruments.

Alternatively, in an embodiment, and in accordance with this disclosure, it is contemplated that transducer 26 (or core 29) may self-orient due to application of a magnetic field thereto, such as, for example, by a magnetic orientation system (not shown). Such a magnetic orientation system is configured to align or orient transducer 26 with a plumb to gravity axis "Z'" (e.g., the core 29 is in an upright orientation) via application of a magnetic field thereto, or in response to receipt of a magnetic field therefrom. It is contemplated that application of a magnetic field to transducer 26 may effect one end of core 29, or one end of core 29 may generate a magnetic field for sensing by receiver or the like.

While an embodiment of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A transponder for use in a surgical environment and for detection by a detection system, the transponder, comprising:
    an encapsulant defining a cavity;
    a suspension medium contained within the cavity of the encapsulant; and
    a core contained within the cavity of the encapsulant, the core including:
        a ferrite rod having a first end and a second end, and defining a longitudinal axis between the first end and the second end, wherein the longitudinal axis of the rod defines an axis of sensitivity of the transponder;
        a head supported on the second end of the rod, the rod and the head configured to define a center of gravity proximate the second end or in the head, wherein the center of gravity is disposed along the longitudinal axis of the rod;
        a conductive coil wrapped around the rod; and
        a capacitor coupled to the conductive coil;
    wherein the cavity of the encapsulant and the core are sized such that the core self-orients itself in multiple axes of rotation, and wherein the axis of sensitivity of the transponder is parallel with a plumb to gravity axis.

2. The transponder according to claim 1, wherein the ferrite rod, the conductive coil and the capacitor form a series inductor/capacitor circuit.

3. The transponder according to claim 1, wherein the capacitor is located proximate the second end of the ferrite rod.

4. The transponder according to claim 1, wherein the encapsulant is fabricated from a bio-inert plastic.

5. The transponder according to claim 1, wherein the cavity of the encapsulant has a spherical internal profile.

6. The transponder according to claim 1, wherein the suspension medium includes a pure silicone fluid, a silicone gel, or a water methyl cellulose mixture.

7. The transponder according to claim 1, wherein the head of the core has a hemi-spherical outer profile.

8. A transponder for use in a surgical environment and for detection by a detection system, the transponder, comprising:
    an encapsulant defining a cavity;
    a suspension medium contained within the cavity of the encapsulant;
    a core contained within the cavity of the encapsulant, the core including:
        a rod having a first end and a second end, and defining a longitudinal axis between the first end and the second end, wherein the longitudinal axis of the rod defines an axis of sensitivity of the transponder, wherein the core defines a center of gravity closer to the second end of the rod as compared to the first end of the rod, and wherein the center of gravity is disposed along the longitudinal axis of the rod;
        a conductive coil wrapped around the rod; and
        a capacitor coupled to the conductive coil;
    wherein the cavity of the encapsulant and the core are sized such that the core self-orients itself in multiple axes of rotation, and wherein the axis of sensitivity of the transponder is parallel with a plumb to gravity axis.

9. The transponder according to claim 8, wherein the rod is fabricated from a ferrous material.

10. The transponder according to claim 9, wherein the rod, the conductive coil and the capacitor form a series inductor/capacitor circuit.

11. The transponder according to claim 9, wherein the core includes a head supported on the second end of the rod.

12. The transponder according to claim 11, wherein the head of the core has a hemi-spherical outer profile.

13. The transponder according to claim 9, wherein the capacitor is located proximate the second end of the rod.

14. The transponder according to claim 9, wherein the encapsulant is fabricated from a bio-inert plastic.

15. The transponder according to claim 9, wherein the cavity of the encapsulant has a spherical inner profile.

16. The transponder according to claim 9, wherein the suspension medium includes a pure silicone fluid, a silicone gel, or a water methyl cellulose mixture.

17. A surgical article for placement in a cavity of a patient during surgery, the surgical article comprising:
a deformable object capable of absorbing body fluid; and
a transponder connected to the deformable object, wherein the transponder includes:
an encapsulant defining a cavity;
a suspension medium contained within the cavity of the encapsulant; and
a core contained within the cavity of the encapsulant, the core including:
a ferrite rod having a first end and a second end, and defining a longitudinal axis between the first end and the second end, wherein the longitudinal axis of the rod defines an axis of sensitivity of the transponder, wherein the core defines a center of gravity closer to the second end of the rod as compared to the first end of the rod, and wherein the center of gravity is disposed along the longitudinal axis of the rod;
a conductive coil wrapped around the rod; and
a capacitor coupled to the conductive coil;
wherein the cavity of the encapsulant and the core are sized such that the core self-orients itself in multiple axes of rotation, and wherein the axis of sensitivity of the transponder is parallel with a plumb to gravity axis.

18. The surgical article according to claim 17, wherein the core of the transducer includes a head supported on the second end of the rod.

19. The surgical article according to claim 18, wherein the suspension medium includes a pure silicone fluid, a silicone gel, or a water methyl cellulose mixture.

20. The surgical article according to claim 17, wherein the cavity of the encapsulant has a spherical inner profile.

* * * * *